United States Patent [19]
Perrino

[11] Patent Number: 5,733,314
[45] Date of Patent: Mar. 31, 1998

[54] PORTABLE SOLAR TANNING SPA

[76] Inventor: Joseph M. Perrino, 1210 Morts Pass, Wyoming, Ohio 45215

[21] Appl. No.: 668,366

[22] Filed: Jun. 17, 1996

[51] Int. Cl.[6] .................................................. A61N 5/06
[52] U.S. Cl. ........................................ 607/91; 607/95
[58] Field of Search .......................... 607/80, 81, 88, 607/90, 91, 94, 95; 5/417, 419, 420; 135/91, 93, 100; 16/319

[56] References Cited

U.S. PATENT DOCUMENTS

| | | | |
|---|---|---|---|
| 407,434 | 7/1889 | Evans | 607/95 |
| 3,244,186 | 4/1966 | Thomason et al. | 135/91 |
| 3,404,696 | 10/1968 | Filho | 135/5 |
| 3,461,890 | 8/1969 | Goodrich | 135/1 |
| 3,812,616 | 5/1974 | Koziol | 47/17 |
| 3,848,279 | 11/1974 | Ipsen, Jr. | 5/113 |
| 3,855,643 | 12/1974 | Sanford et al. | 4/172.12 |
| 4,097,944 | 7/1978 | Yulish | 5/344 |
| 4,292,708 | 10/1981 | Stefanovic | 16/319 |
| 4,320,744 | 3/1982 | Fodor et al. | 607/95 |
| 4,476,593 | 10/1984 | Fanselow et al. | 5/417 |
| 4,525,884 | 7/1985 | Tolley | 607/95 |
| 4,582,062 | 4/1986 | Albini | 128/396 |
| 4,739,763 | 4/1988 | Parsell | 607/81 |
| 4,860,777 | 8/1989 | Orlando | 135/87 |
| 4,989,600 | 2/1991 | Collier | 607/95 |
| 5,059,463 | 10/1991 | Peters | 428/65 |
| 5,088,514 | 2/1992 | House et al. | 135/107 |
| 5,387,230 | 2/1995 | Minor | 607/95 |
| 5,446,580 | 8/1995 | Collins | 359/350 |

FOREIGN PATENT DOCUMENTS

| | | | |
|---|---|---|---|
| 2030815 | 5/1992 | Canada | 607/95 |

*Primary Examiner*—Jennifer Bahr
*Assistant Examiner*—Bryan K. Yarnell
*Attorney, Agent, or Firm*—Smith, Brandenburg, Freese & Knochelmann, P.L.C.; George P. Brandenburg; Mark F. Smith

[57] ABSTRACT

A portable solar tanning spa having a longitudinally extending first half section and a longitudinally extending second half section, each being formed of a light transparent material. The first half section and the second half section are rotatably connected such that the second half section may rotate into a position parallel with the first half section to allow the user to enter and exit as desired. In a preferred embodiment of the present invention, the longitudinally extending first half section and the longitudinally extending second half section are arranged in a vertical position and are pivotally connected to the rim of a back member to allow the first half section and the second half section to swing outwardly into an open position and inwardly into a closed position. In another preferred embodiment of the present invention, the first half section and the second half section form a cylindrical enclosure having an opening for receiving a door to allow the user to enter or exit the spa as desired.

15 Claims, 6 Drawing Sheets

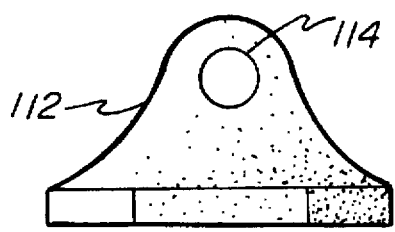
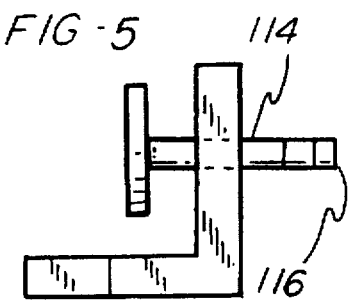
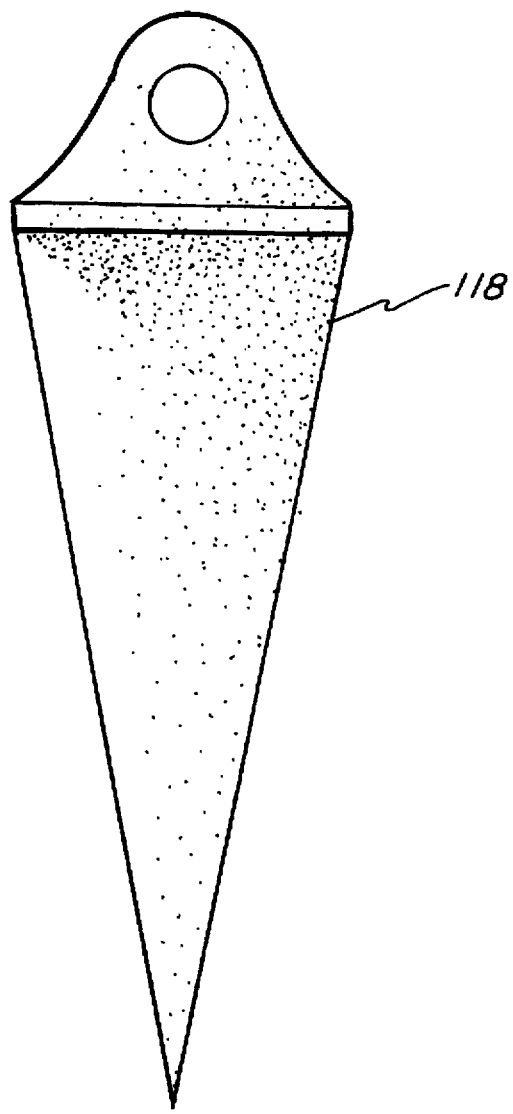
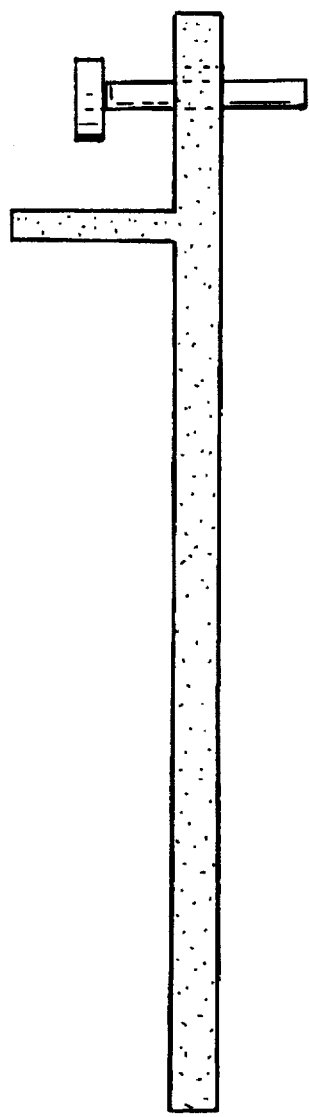

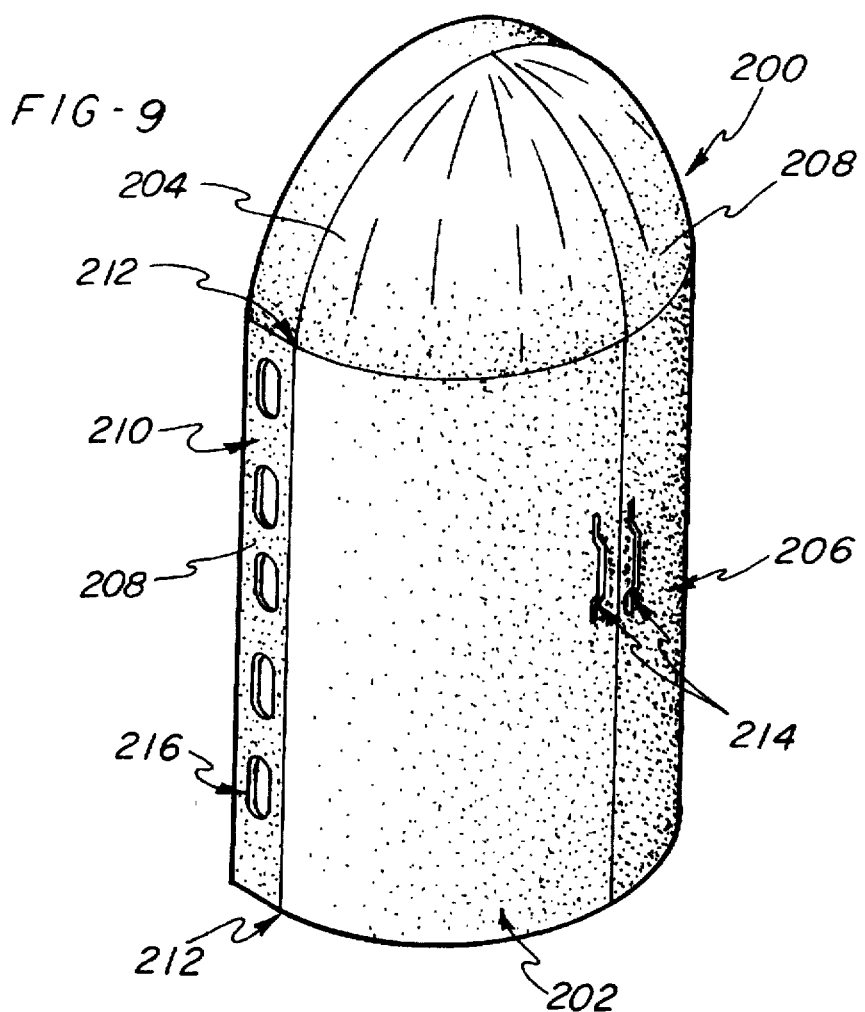
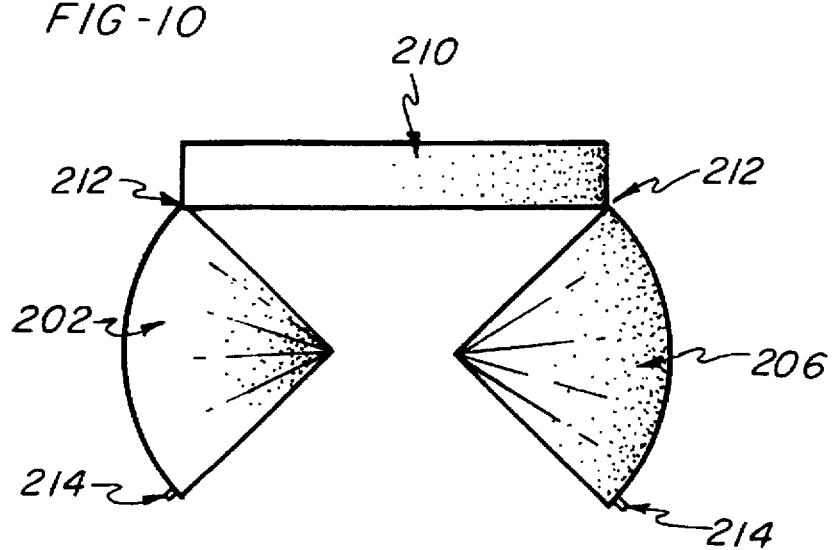

PORTABLE SOLAR TANNING SPA

BACKGROUND OF THE INVENTION

This invention relates to tanning spas and, more particularly, to a portable solar tanning spa which can be adapted to effect tanning and privacy for the user.

Various designs have been developed for portable solar tanning spas. One such prior art tanning spa is shown in U.S. Pat. No. 5,446,580, which discloses a compact selectively transmissive screen which is erected over portions of a user's body. Another prior art tanning spa is shown in U.S. Pat. No. 5,088,514, which discloses a portable tanning and screening apparatus having a panel with a reflective surface for directing or blocking sun light. Such potable tanning spas, however, do not teach the basic individual concepts utilized to produce the present invention or contain the advantages inherent in the present invention.

SUMMARY OF THE INVENTION

The present invention is directed to a portable solar tanning spa comprising a longitudinally extending first half section and a longitudinally extending second half section, each being formed of a light transparent material. The first half section and the second half section are rotatably connected such that the second half section may rotate into a position parallel with the first half section to allow the user to enter and exit as desired.

In another preferred embodiment of the present invention, the longitudinally extending first half section and the longitudinally extending second half section are arranged in a vertical position and are pivotally connected to the rim of a back member to allow the first half section and the second half section to swing outwardly into an open position and inwardly into a closed position.

In another preferred embodiment of the present invention, the first half section and the second half section form a cylindrical enclosure having an opening for receiving a door to allow the user to enter or exit the spa as desired.

The portable solar tanning spa of the present invention may further comprise air vents capable of opening and closing to allow for the comfort of the user, and a light reflective covering having an up position for reflecting the sun's rays away from the user and a darker down side for absorbing the sun's rays.

A primary object of the present invention, therefore, is to provide a new and novel healthful solar tanning spa.

Another primary object of the present invention is to provide a portable solar tanning spa with means for allowing the user to enjoy the heat from the sun while blocking cool air.

Another primary object of the present invention is to provide a portable solar tanning spa for allowing the user to tan without being subjected to all of the sun's harmful rays.

Another primary object of the present invention is to provide a portable solar tanning spa which can be easily manufactured in a variety of sizes and shapes allowing the user multiple selections for use.

Another primary object of the present invention is to provide a portable solar tanning spa which is adaptable to a multiplicity of diverse uses.

Another primary object of the present invention is to provide a portable solar tanning spa with means for providing adequate ventilation.

These and other objects, features and advantages of the invention will be more fully understood from the following detailed description, taken in conjunction with the accompanying drawings and examples, all of which are intended to be typical of, rather than in any way limiting on the scope of the present invention.

BRIEF DESCRIPTION OF THE DRAWINGS

For a better understanding of the present invention, reference may be had to the following descriptions, taken in conjunction with the accompanying drawings wherein:

FIG. 4 is a side view of a conventional rotating and tightening assembly;

FIG. 5 is a front view of the conventional rotating and tightening assembly shown in FIG. 4;

FIG. 6 is a side view of the conventional rotating and tightening assembly of FIGS. 4 and having a bracket for penetrating into the surface of the ground.

FIG. 9 is a perspective view of the portable solar tanning spa constructed in accordance with another preferred embodiment of the invention;

FIG. 10 is a top view of the subject invention of FIG. 9 shown in an open position;

DESCRIPTION OF THE PREFERRED EMBODIMENTS

Referring now more particularly to the drawings wherein like parts, in each view, have like numbers, a description of the preferred embodiments of the present invention follows.

Figure 1:
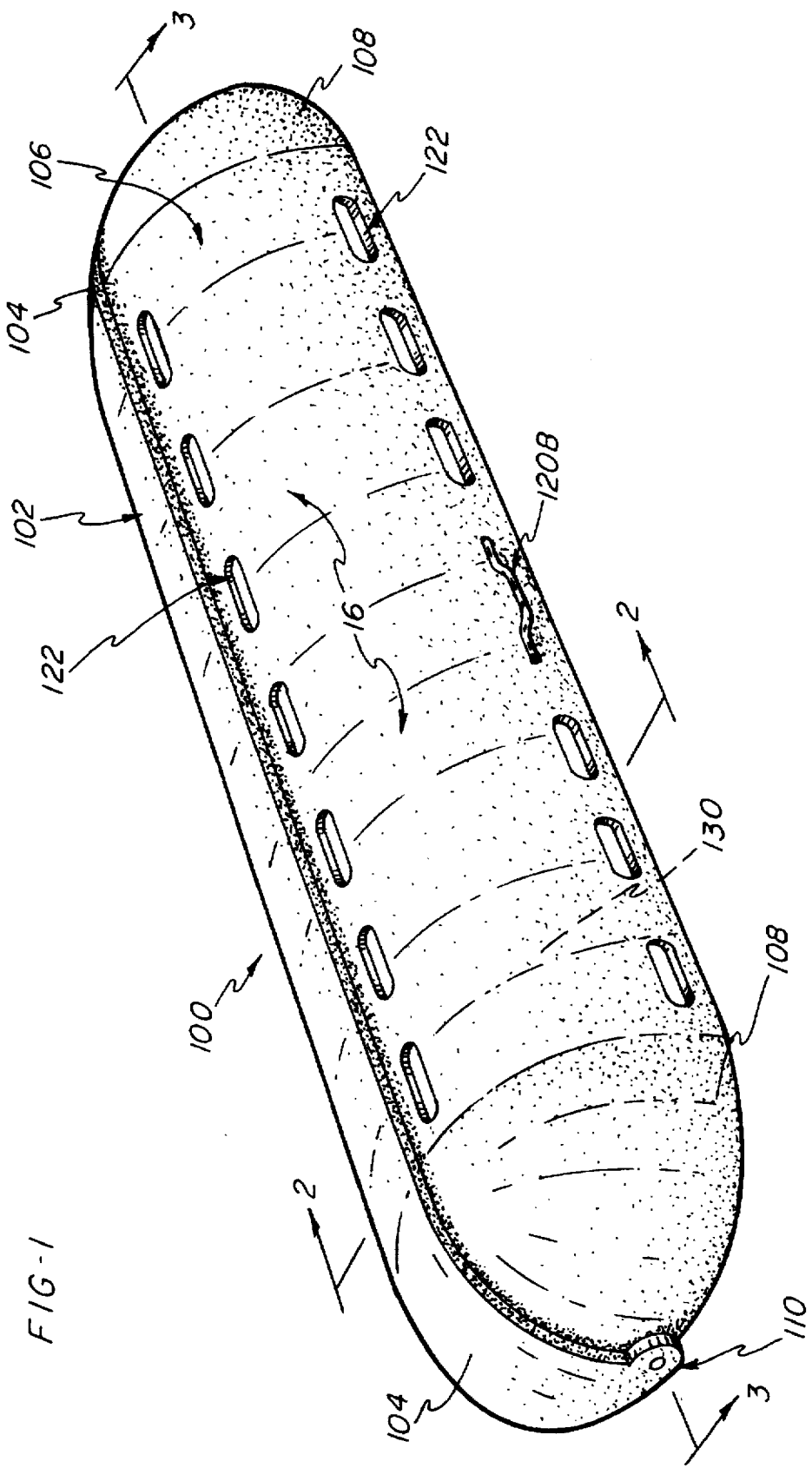
FIG. 1 is a perspective view of a portable solar tanning spa constructed in accordance with a preferred embodiment of the invention.
Figure 2:
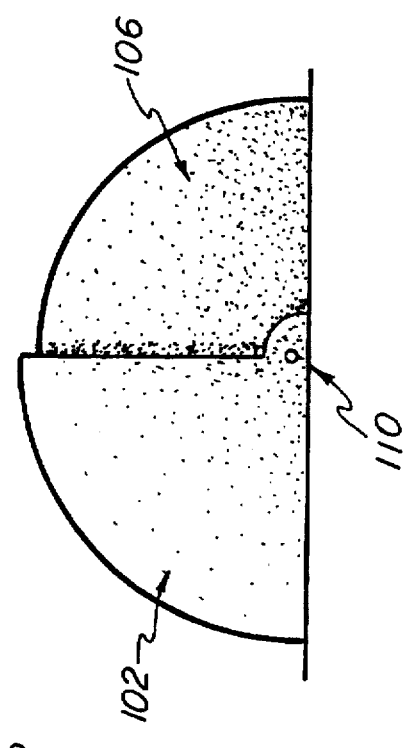
FIG. 2 is a sectional view of the subject invention taken along line 2—2 of FIG. 1.
Figure 3:
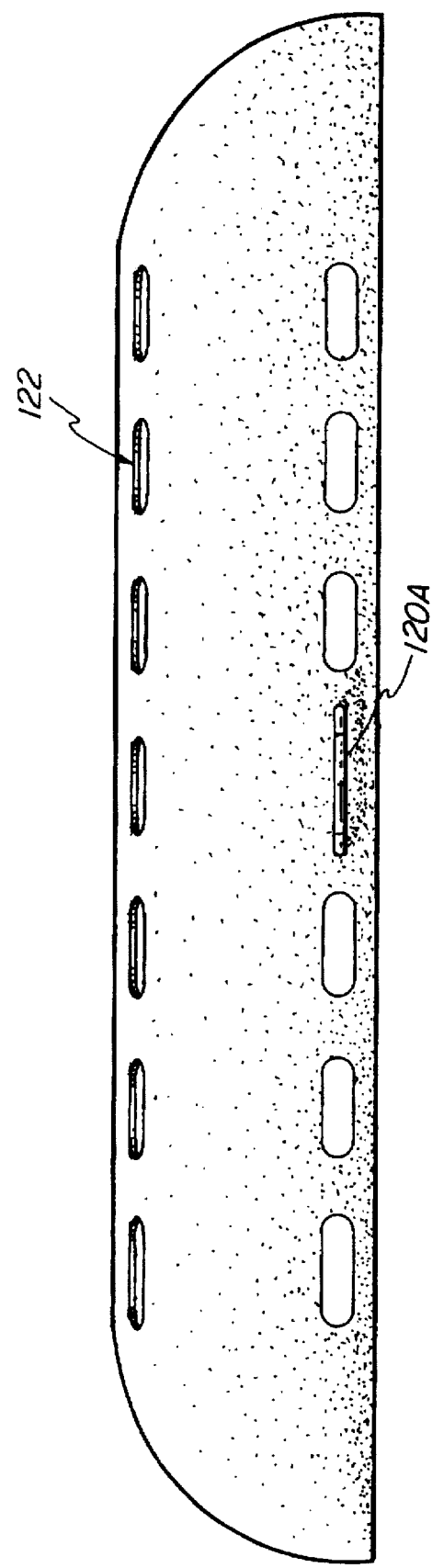
FIG. 3 is a sectional view of the subject invention taken along line 3—3 of FIG. 1.

FIGS. 1 through 3 illustrate a preferred embodiment of a portable solar tanning spa of the present invention. The portable tanning spa, generally designated 100, comprises a longitudinally extending first half section 102 having first and second inwardly curving ends 104, and a longitudinally extending second half section 106 having first and second inwardly curving ends 108. The respective ends of the first and second half sections 104, 108 are rotatably connected together by conventional rotating and tightening assemblies 110, such as shown in FIGS. 4 and 5, having a clamp 112 with a threaded bore 114 for receiving a bolt 116 for tightening or loosening the point of rotation. The longitudinally extending second half section 106 is slightly smaller than longitudinally extending first half section 102, as shown in FIG. 2, such that the second half section 106 may rotate into position parallel with the first half section 102. Such nesting of the second half section 106 within the first half section 102 allows the user to enter and exit easily and comfortably from the portable solar tanning spa 100. In order to provide additional stability to the portable solar tanning spa 100, such as for windy conditions, the rotating and tightening assemblies 110 may be provided with brackets 118 (FIG. 6) for penetrating into the surface of the ground.

In operation, the user rotates the second half section 106 into either an open or closed condition by use of a inner and outer handles 120A and 120B positioned on the longitudinally extending second half section 106. The inner handle 120A extends generally inwardly from the second half section 106 and the outer handle 120B extends outwardly from the second half section 106 to aid the user while exiting or entering the portable solar tanning spa 100.

The portable solar tanning spa 100 is further provided with a plurality of air vents 122 which are capable of opening and closing to provide for the comfort of the user. For example, on colder days, the vents 122 may be closed to prevent heat from escaping out of the portable solar tanning spa 100 while on hotter days they may be opened to permit warm air to escape out of the portable solar tanning spa 100 and to permit cooler air to enter into the portable solar tanning spa 100.

Additionally it should be apparent to one skilled in the art, the user may elect on hotter days to rotate and lock the longitudinally extending second half section 106, using the rotating and tightening assembly 110, into a nesting position with the longitudinally extending first half section 102 in order to have an additional layer of opaque sun screen between the user and the sun's rays.

Figure 7:
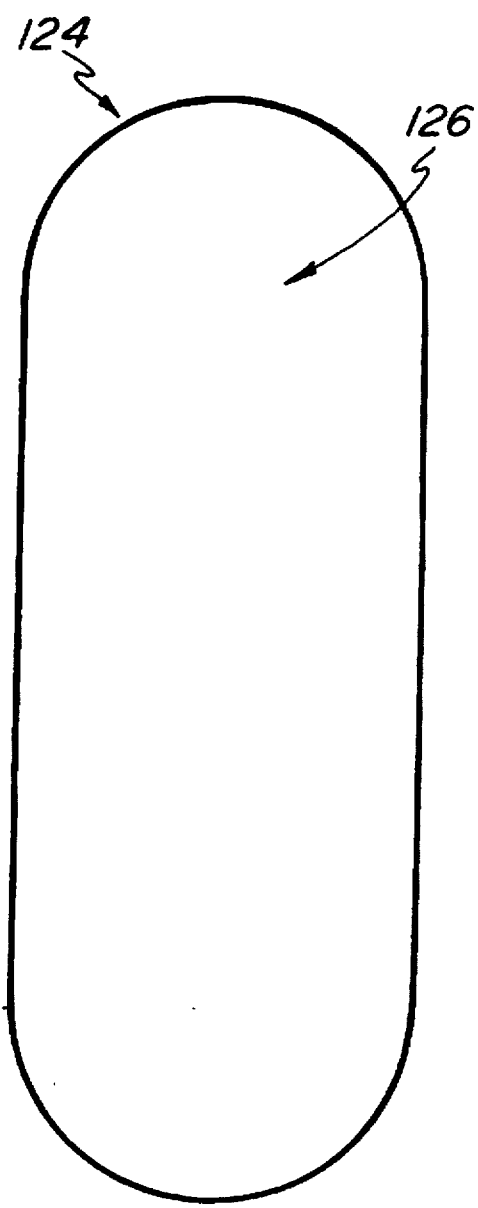
FIG. 7. is a top view of the floor or ground covering of the subject invention depicted in FIG. 1 showing a light reflective surface.
Figure 8:
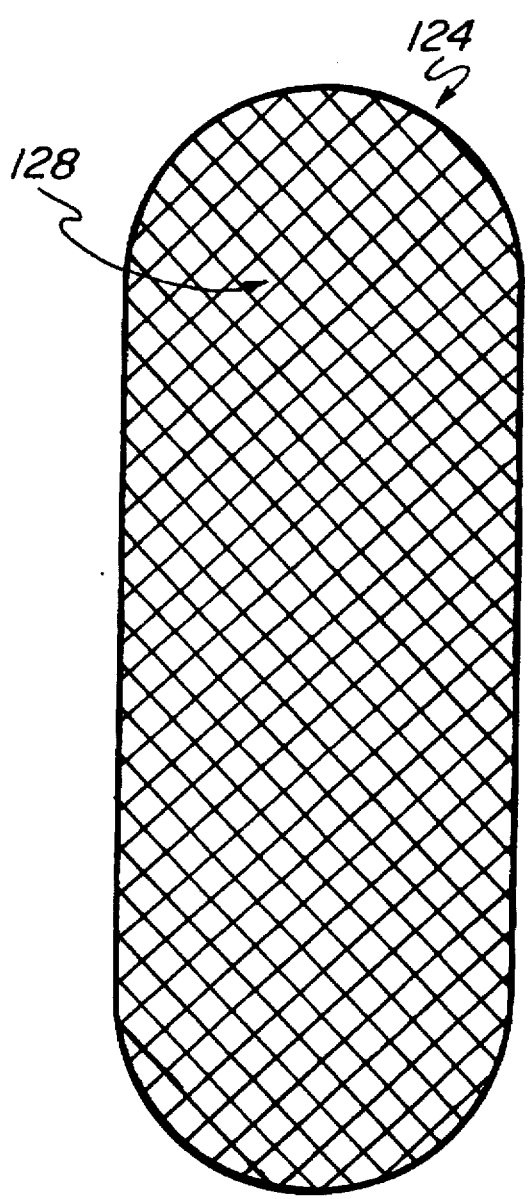
FIG. 8 is it top view of the floor or ground covering of the subject invention depicted in FIG. 1 showing a light absorbing surface.

In addition to the use of the vents 122 and the positioning of spa 100 to control the user's environment, a floor or ground covering 124, as shown in FIGS. 7 and 8, may be provided having a light reflective surface 126 (FIG. 7) and a light absorbing surface 128 (FIG. 8). In use, the light reflective surface 126 of the ground covering 124 is placed in the up position on hot days, such that the sun's rays are reflected away from the user, and on cooler days, the light absorbing surface 128 is placed in the up position to absorb the sun's warmth. It should be apparent to one skilled in the art that the particular size and shape of the floor or ground covering may be selected for the convenience of the user.

The first half section 102 and the second half section 106 are formed of a relatively rigid, light transparent, material. It should be apparent to one skilled in the art that the material forming the first and second half sections may be selected from a variety of commercially available plastics, glasses or screens or combinations thereof which will admit the healthful rays from the sun to provide warmth and or tanning ability to the user. In addition, such materials may be selected to provide varying degrees of sun blocking capability throughout the visible and the ultra violate ranges. It should also be apparent to one skilled in the art that the first half section 102 and the second half section 106 may be reenforced by a plurality of support ribs 130 thereby permitting the use of a thinner and more flexible light transparent material.

An alternate embodiment of the portable solar tanning spa 200 of the present invention is shown in FIGS. 9 and 10 comprising a longitudinally extending first half section 202 having an inwardly curving end 204, a longitudinally extending second half section 206 having an inwardly curving end 208 are arranged in the vertical position to allow the user to be in a standing or sitting position rather than in a prone position as preferred in the embodiment shown in FIG. 1. The first half section 202 and the second half section 206 are connected to the outer rim 208 of a stationary back member 210 by conventional hinge assemblies 212 to permit the first and second half sections to swing outwardly to an open position and inwardly to a closed position. Handles 214, extending generally outwardly from and inwardly from their respective half sections 202 and 206, are provided for ease in swinging the half sections into open and closed positions. Air vents 216, capable of opening and closing, are provided along the rim 208 of the back member 210 to allow for the comfort of the user.

Figure 12:
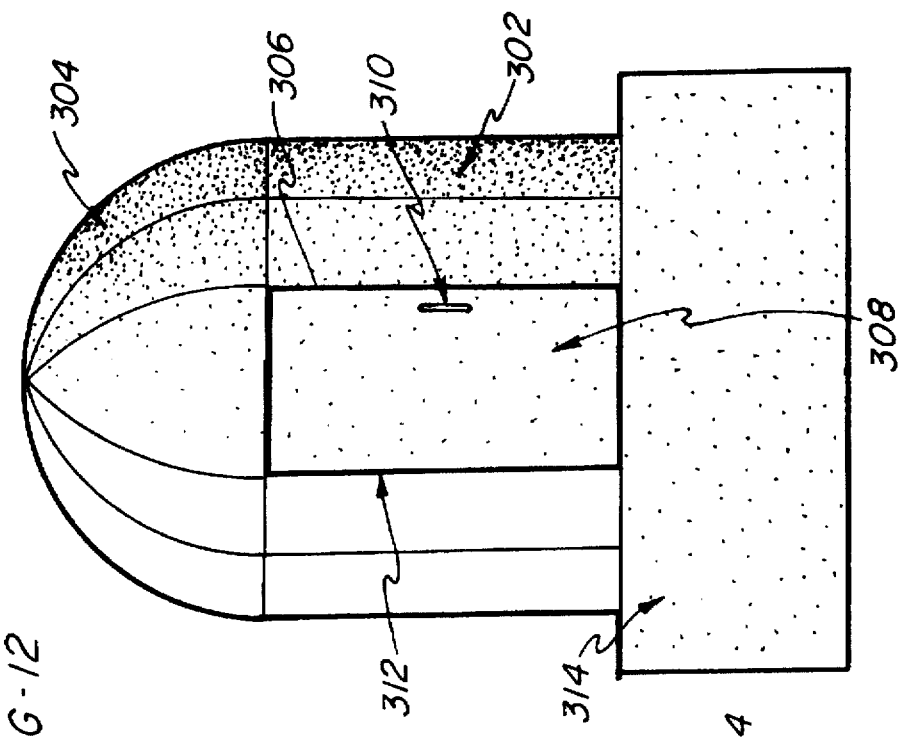
FIG. 12 is a front view of the subject invention of FIG. 11.
Figure 11:
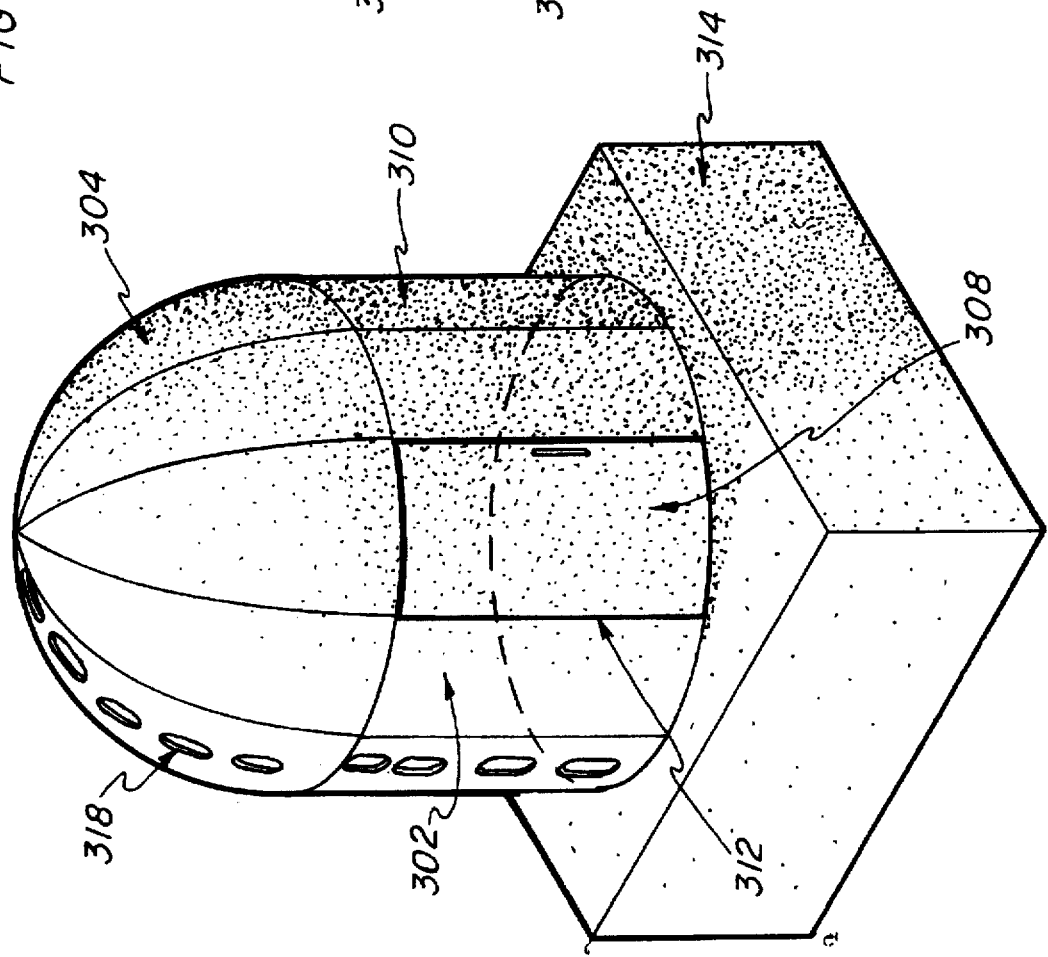
FIG. 11 is a perspective view of the portable solar tanning spa constructed in accordance with another preferred embodiment of the invention.

In another preferred embodiment, shown in FIGS. 11 and 12, of portable solar tanning spa 300 of the subject invention, the first half section and the second half section form a generally cylindrical enclosure 302 having an inwardly converging upper section 304 and an opening 306 for receiving a door 308, having a handle 310, which is pivotally attached to the cylindrical enclosure 302 by a hinge 312. The portable tanning spa 300 is typically positioned on a base 314 for rigidly securing the spa.

It should be apparent to one skilled in the art that the preferred embodiments of the portable solar tanning spa shown in FIGS. 9 and 10 and FIGS. 11 and 12 comprise all of the uses, modifications and advantages of the preferred embodiment of the portable tanning spa shown in FIGS. 1 through 8 and previously described. In particular, the first and second half sections of the portable solar tanning spa are formed of a relatively rigid, light transmitting material; support ribs may be provided for reinforcing the first and second half sections to permit the use of thinner, more flexible light transparent material; and floor or ground covering may be provided having a light reflective surface and a light absorbing surface. It should also be apparent to one skilled in the art that a plurality of tent stakes may be positioned about the portable tanning spa to secure the spa to the ground. In addition, the portable solar tanning spa may be provided with conventional attachments for securing cords to further anchor the portable solar tanning spa to the ground.

Although this invention has been shown and described with respect to detailed embodiments thereof, it will be understood by those skilled in the art that various changes in form and detail thereof may be made without departing from the spirit and scope of the claimed invention.

What is claimed is:

1. A portable solar tanning spa comprising:
    a semi-cylindrical section having
    a longitudinally extending first half section; and
    a longitudinally extending second half section;
    wherein said first half section and said second half section are each formed of a light transparent material;
    wherein said first half section and said second half section are rotatably connected such that said second half section rotates into a position parallel with said first half section.

2. The portable solar tanning spa of claim 1 wherein said second half section further comprising a plurality of air vents.

3. The portable solar tanning spa of claim 1 wherein said second half section further comprising handle means for rotating said second half section into and out of a position parallel with said first half section.

4. The portable solar tanning spa of claim 1 wherein said first half section and said second half section each comprise a plurality of ribs.

5. The portable solar tanning spa of claim 1 further comprising a ground covering having a light reflective surface and a light absorbing surface.

6. The portable solar tanning spa of claim 1 further comprising a rotating and tightening assembly for locking said second half section into a nesting position with said first half section.

7. The portable solar tanning spa of claim 6 wherein said rotating and tightening assembly comprises a bracket for penetrating into the surface of the ground to effect additional stability.

8. A portable solar tanning spa comprising:

a longitudinally extending first half section;

a longitudinally extending second half section; and a back member;

wherein said first half section and said second half section are each formed of a light transparent material; and wherein said first half section and said second half section are each pivotally connected to said back member to allow said first half section and said second half section to swing independently from each other in an outward direction into an open position and in an inward direction into a closed position.

9. The portable solar tanning spa of claim 8 wherein said second half section further comprising a plurality of air vents.

10. The portable solar tanning spa of claim 8 wherein said first half section and said second half section each comprise a plurality of ribs.

11. The portable solar tanning spa of claim 8 further comprising a ground covering having a light reflective surface and a light absorbing surface.

12. A portable solar tanning spa comprising:

a cylindrical enclosure having an opening for receiving a door;

a door pivotally attached to said cylindrical enclosure; and a base for supporting said cylindrical enclosure;

wherein said cylindrical enclosure is formed of a light transparent material.

13. The portable solar tanning spa of claim 12 further comprising a plurality of air vents.

14. The portable solar tanning spa of claim 12 wherein said cylindrical enclosure comprise a plurality of ribs.

15. The portable solar tanning spa of claim 12 further comprising a ground covering having a light reflective surface and a light absorbing surface.

* * * * *